(12) United States Patent
Dovichi et al.

(10) Patent No.: US 10,416,115 B2
(45) Date of Patent: Sep. 17, 2019

(54) SYSTEM FOR CAPILLARY ELECTROPHORESIS FOR PEPTIDE AND PROTEIN ANALYSIS

(71) Applicant: University of Notre Dame du Lac, Notre Dame, IN (US)

(72) Inventors: Norman Dovichi, South Bend, IN (US); Guijie Zhu, South Bend, IN (US); Liangliang Sun, South Bend, IN (US)

(73) Assignee: University of Nortre Dame du Lac, South Bend, IN (US)

( * ) Notice: Subject to any disclaimer, the term of this patent is extended or adjusted under 35 U.S.C. 154(b) by 370 days.

(21) Appl. No.: 15/187,482

(22) Filed: Jun. 20, 2016

(65) Prior Publication Data

US 2017/0363576 A1    Dec. 21, 2017

(51) Int. Cl.
*G01N 27/447*      (2006.01)
*G01N 27/26*       (2006.01)
(Continued)

(52) U.S. Cl.
CPC ..... *G01N 27/44752* (2013.01); *B05D 3/0254* (2013.01); *B05D 3/0493* (2013.01); *B05D 5/00* (2013.01); *B05D 7/22* (2013.01); *B05D 7/222* (2013.01); *C03C 17/004* (2013.01); *C03C 17/28* (2013.01); *C03C 17/38* (2013.01); *C03C 23/007* (2013.01); *G01N 27/26* (2013.01); *G01N 27/447* (2013.01); *G01N 27/44704* (2013.01);
(Continued)

(58) Field of Classification Search
CPC ...... G01N 27/00; G01N 27/26; G01N 27/447; G01N 27/44704; G01N 27/44752; B05D 3/0254; B05D 3/0493; B05D 5/00; B05D 7/22; B05D 7/222; B05D 2203/30; B05D 2203/35; B05D 2254/04; B05D 2259/00; B05D 2502/005; B05D 2505/00; C03C 17/004; C03C 17/28; C03C 17/38; C03C 23/007; C03C 2203/52; C03C 2218/11; C03C 2218/32
USPC .................................................. 427/230, 238
See application file for complete search history.

(56) References Cited

U.S. PATENT DOCUMENTS 4,997,537 A *  3/1991  Karger ............ G01N 27/44721
                                                    204/453
5,503,722 A    4/1996  Guttman
(Continued)

OTHER PUBLICATIONS

Doherty et al., "Microchannel wall coatings for protein separations by capillary and chip electrophoresis," Electrophoresis 2003, 24, 34-54. (Year: 2003).*
Horvath et al., "Polymer Wall Coatings for Capillary Electrophoresis", Electrophoresis, 2001, pp. 644-655, vol. 22; Wiley-VCH Verlag GmbH.
(Continued)

*Primary Examiner* — William P Fletcher, III
(74) *Attorney, Agent, or Firm* — Haukaas Fortius PLLC; Michael H. Haukaas

(57) ABSTRACT

A method of coating the inside wall of a capillary with a polymeric material for capillary electrophoresis is disclosed. The method can include introducing a catalyst-free solution of a monomer and initiator, wherein the monomer is present in about 1-10% (w/v) and the initiator is present in 0.1-1% (w/v), into a capillary and thermally initiating polymerization of the monomer thereby providing a capillary comprising an internal polymeric coating for separating, identifying, and quantifying components of an analyte.

19 Claims, 8 Drawing Sheets

See Fig. 1

(51) Int. Cl.
    B05D 7/22       (2006.01)
    B05D 5/00       (2006.01)
    B05D 3/02       (2006.01)
    B05D 3/04       (2006.01)
    C03C 17/00      (2006.01)
    C03C 17/38      (2006.01)
    C03C 23/00      (2006.01)
    C03C 17/28      (2006.01)
(52) U.S. Cl.
    CPC ...... B05D 2203/30 (2013.01); B05D 2203/35 (2013.01); B05D 2254/04 (2013.01); B05D 2259/00 (2013.01); B05D 2502/005 (2013.01); B05D 2505/00 (2013.01); C03C 2203/52 (2013.01); C03C 2218/11 (2013.01); C03C 2218/32 (2013.01)

(56) References Cited

U.S. PATENT DOCUMENTS

| | | | |
|---|---|---|---|
| 2005/0249882 A1 | 11/2005 | Liu et al. | |
| 2006/0108225 A1* | 5/2006 | Carson | G01N 27/44747 204/455 |
| 2014/0209461 A1* | 7/2014 | Lau | G01N 27/44747 204/451 |

OTHER PUBLICATIONS

Zhu et al., "Thermally-Initiated Free Radical Polymerization for Reproducible Production of Stable Linear Polyacrylamide Coated Capillaries, and Their Application to Proteomic Analysis Using Capillary Zone Electrophoresis-Mass Spectrometry", Talanta, 2016, published Jun. 20, 2015; pp. 839-843, vol. 146; Elsevier B.V.

* cited by examiner

SYSTEM FOR CAPILLARY ELECTROPHORESIS FOR PEPTIDE AND PROTEIN ANALYSIS

GOVERNMENT SUPPORT

This invention was made with government support under Grant No. R01GM096767 awarded by the National Institutes of Health. The government has certain rights in the invention.

BACKGROUND OF THE INVENTION

Historically, chemical analysis of charged analytes has been carried out using slow, expensive, low resolution, and solvent, gas, and instrumentation intensive techniques such as ion-exchange chromatography, atomic absorption and inductively coupled plasma emission spectroscopy.

More recently, capillary electrophoresis has become an important tool for chemical analysis of charged analytes as well as a wide variety of other separation problems. The introduction and development of capillaries, small-diameter chromatographic columns containing an internal stationary phase, have played an important part in the advancement of many areas of science and industry.

In capillary zone electrophoresis (CZE) analyte components move from an injector end of a capillary to a detector end of a capillary under the influence a voltage difference applied across the length of the capillary. Because of the different mass-to-charge ratios (m/z) of analyte components, the individual components of the analyte move through the column with different velocities. This difference in movement through the capillary leads to the physical separation of the components of the analyte into individual electrophoretic zones. The separated components of the analyte are then detected instrumentally as they are eluted from the capillary.

Advantages of CZE include a high theoretical plate number, about 3-10 times higher than other analytical techniques such as high performance liquid chromatography (HPLC) owing to the band moving in a flat rather than a parabolic profile, no mechanical pump, rapid analysis time, low cost per test, low solvent requirements, full automation, and ability to modify the selectivity of the separation simply by adding additives to the buffer to alter the velocity of some analytes.

However, disadvantages of CZE include poor sensitivity of absorbency detection and problems with sample matrix and sample adsorption to the capillary. Many of these issues are the direct result of the current method of manufacturing the capillary columns. Currently polymerization of the internal stationary phase is initiated external from the capillary resulting in an inconsistent stationary phase profile, limiting capillary length, sensitivity, and resolution. Enhancing these characteristics of the capillary would be a great advance in chromatography.

Capillary zone electrophoresis is an attractive alternative to liquid chromatography, particularly in proteomics research. CZE provides rapid and efficient separation of biological molecules. Uncoated capillaries generate high electroosmotic flow that leads to rapid separations, but with a short separation window that limits the peptide and protein identification in analysis of complex proteomes. Instead, proteomic analysis by CZE requires the use of capillaries that have had their interior uniformly coated with a polymer, which both suppresses electroosmotic flow and minimizes peptide interaction with the wall.

A capillary coating of linear polyacrylamide (LPA) is commonly used in CZE separations. Typically, the LPA coating is produced by covalently bonding acrylamide monomer to the inner wall of the capillary. The capillary is first treated with a vinyl-silane to covalently graft a double bond to the silica capillary wall. Next, a polymerization mixture is prepared by mixing a monomer (e.g., acrylamide), polymerization initiator (e.g., ammonium persulfate (APS)), and water in a tube, external to the capillary. The solution is then degassed by $N_{2(g)}$ to remove oxygen. Tetramethylethylenediamine (TEMED) is then added as a catalyst to the mixture and the polymerization reaction commences. The polymerizing mixture must then rapidly be introduced into the pretreated capillary. The time between the addition of TEMED and introduction of the mixture to the capillary critically affects the performance and reproducibility of the capillary. In addition, a special device is typically required to perform the step of introducing the polymerizing mixture to the capillary. This method results in a capillary coating that is not uniform throughout the capillary and exposed column surface, which lacks uniformity from batch to batch, has limited capillary length, and poor capillary resolution and reproducibility.

Accordingly, there is a need for a capillary with improved coating uniformity, reproducibility, resolution, and higher separation efficiency. Additionally, there is a need for such a capillary capable of being fabricated in long columns/with increased length compared to currently available capillaries. The present invention describes a novel method of producing a capillary that provides all of the above-mentioned desirable characteristics through a simple procedure carried out under mild thermal conditions.

SUMMARY

The invention provides a novel catalyst free method for preparation of stable and reproducible linear polyacrylamide (LPA) coated capillaries. In the present invention a degassed polymerization solution containing a monomer, an initiator, and water is introduced into the capillary via vacuum. The capillary is then heated to thermally decompose the initiator, thereby allowing the polymerization reaction to proceed. Because the polymerization is thermally initiated after the mixture is introduced into the capillary, the polymerization process can be controlled precisely and initiated simultaneously along the length of the capillary.

Proteomic analysis using CZE is typically performed with LPA coated capillaries. These capillaries minimize the adsorption of peptides and proteins to the inner wall of the capillary and decrease electroosmosis, which increases the separation capacity. Conventional LPA-coated capillary production is based on the use of TEMED to catalyze the free-radical polymerization that couples acrylamide to a pretreated capillary wall. The treated capillary is filled with a mixture of monomer, TEMED, and ammonium persulfate; with free radical polymerization beginning prior to introduction of the solution to the capillary. This previous method results in significant variation in the properties of LPA-coated capillaries both along the length of the capillary and between lots. This variation is due to differences in the time between initiation of the reaction and the filling of the capillary.

The present invention relates to a method for the generation of stable and reproducible coatings. The monomer and initiator can be mixed and introduced into the capillary without the TEMED catalyst. The mixture is stable and does not begin polymerization at room temperature. The capillary, now filled with the mixture described herein, can then be heated, for example, in a water bath, thereby initiating polymerization. This novel method of coating the inside of a capillary provides an inner coating in a more well-controlled manner.

A mixture of four standard proteins was used to evaluate the coating performance. Compared with commercialized LPA capillaries, the LPA capillaries described herein generate much better separation performance and superior protein peak shape in CZE analysis. Also analyzed was an intact antibody (MW 150 k) by CZE-MS with the LPA capillary described herein in triplicate runs. The intact antibody generated a Gaussian-shaped electrophoresis peak with 1.2% relative standard deviation in migration time and 8.5% in base peak intensity. An automated CZE-MS system was used to generate 97 successive separations of a BSA tryptic digest over 145 hours. Separation efficiency averaged over 100,000 theoretical plates across this period with no systematic variation. The LPA coating protocol had excellent batch-to-batch reproducibility with relative standard deviation in migration time of <7%, and in separation window of <1%.

Accordingly, the present invention provides a method of coating the inside of a capillary with a polymeric material. The inside of the capillary can be coated by introducing a catalyst-free solution of a monomer, present in about 2% to about 10% (w/v), and an initiator, present in about 0.1% to about 10% (w/v), into the capillary. Once introduced into the capillary the capillary is heated thereby thermally initiating polymerization of the monomer and providing a capillary comprising an internal polymeric coating.

In one embodiment, the monomer forms a hydrophilic polymer upon polymerization. In another embodiment the monomer forms a hydrophobic polymer upon polymerization. In yet another embodiment the monomer forms a polymeric coating comprising both hydrophilic and hydrophobic regions/characteristics. In a certain embodiment the monomer is acrylamide.

In one embodiment, the initiator is an oxidizing agent. In some embodiments, the oxidizing agent is a hydrosoluble oxidizing agent. In certain embodiments, the oxidizing agent is soluble in water, ethanol, or a combination of water and ethanol. In some embodiments the initiator is a persulfate such as ammonium persulfate, sodium persulfate, or potassium persulfate. Other suitable oxidizing agents include azo initiators such as azobisisobutyronitrile (AIBN), 2,2'-azobis(2-methylpropionamidine) dihydrochloride, 2,2'-azobis(2-methylpropionitrile), 2,2'-azobis(2-methylbutanenitrile), 4,4'-azobis(4-cyanovaleric acid), 2,2'-azobis(2,4-dimethylvaleronitrile), 1,1'-azobis(cyanocyclohexane), 4,4'-azobis(4-cyanovaleric acid), 1,1'-azobis(n,n-dimethylformamide), 2,2'-azobis(4-methoxy-2,4-dimethylvaleronitrile), 2,2'-azobis(2-methylbutyronitrile), or 2,2'-azobis(2,4,4-trimethylpentane).

In one embodiment, the catalyst-free solution is an aqueous solution. The solution can be introduced into the capillary by vacuum.

In one embodiment, thermally initiating polymerization of the monomer comprises sealing both ends of the capillary and heating the capillary. In a further embodiment the capillary is heated to about 40° C. to about 70° C., or about 45° C. to about 60° C., typically about 50° C. The heating can be for any suitable and effective period of time, for example, at least about two minutes, or about two minutes to about 60 minutes, or about 30 minutes.

In one embodiment, the resolution, $R_s$, of the capillary is improved by a factor of about 1.5 to about 2.5. In various embodiments, the resolution of the capillary is improved by at least a factor of about 2.

In one embodiment, the reproducibility of analyte migration along the capillary is about 3% to about 5% run to run. In a further embodiment, reproducibility of analyte migration along the capillary is about 6% to about 8% batch to batch.

In one embodiment, the relative standard deviation of the separation window is about 0.5% to about 1.5% batch to batch.

The invention also provides a method for separating, identifying and quantifying components of an analyte comprising introducing the analyte into a capillary, wherein the capillary has a proximate end, a distal end, and an interior, wherein the interior of the capillary has been coated with a polymeric coating, the polymeric coating having been introduced via vacuum into the capillary as a solution of a monomer and an initiator, and polymerization of the monomer initiated thermally inside the capillary, migrating the analyte through the capillary, and then detecting analyte components.

In one embodiment the analyte is introduced to the capillary as a liquid, gas, and/or vapor.

In one embodiment the analyte is migrated through the capillary by a pressure differential between the proximate and distal ends of the capillary.

In one embodiment the analyte is migrated through the capillary by an electric potential differential between the proximate and distal ends of the capillary.

In one embodiment the components of the analyte are detected using a detector selected from spectrophotometric, fluorescence, electrochemical, refractive index, coulometry, adsorption, thermal lens, Raman, conductivity, potentiometry, amperometry, and/or mass analyzers.

In one embodiment the monomer is polymerized via homolytic polymerization.

In one embodiment the solution of a monomer and initiator comprises an acrylamide and a persulfate.

The invention also provides a capillary comprising a proximate end comprising an aperture and a distal end comprising an aperture wherein the distal and/or proximate aperture are about 0.08 mm to about 0.7 mm in diameter, an outside of the capillary wherein the outside comprises a flexible material, an inside of the capillary wherein the inside comprises a flexible polymeric material, wherein the flexible polymeric material is thermally polymerized inside the capillary from a catalyst free solution of a monomer and an initiator. The capillary can be anywhere from about 0.1 m to about 100 m in length.

The invention thus provides novel components, intermediates for the preparation of the components, as well as methods of preparing the components. The invention provides the methods described herein for the manufacture of coatings and for the manufacture of capillary columns.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
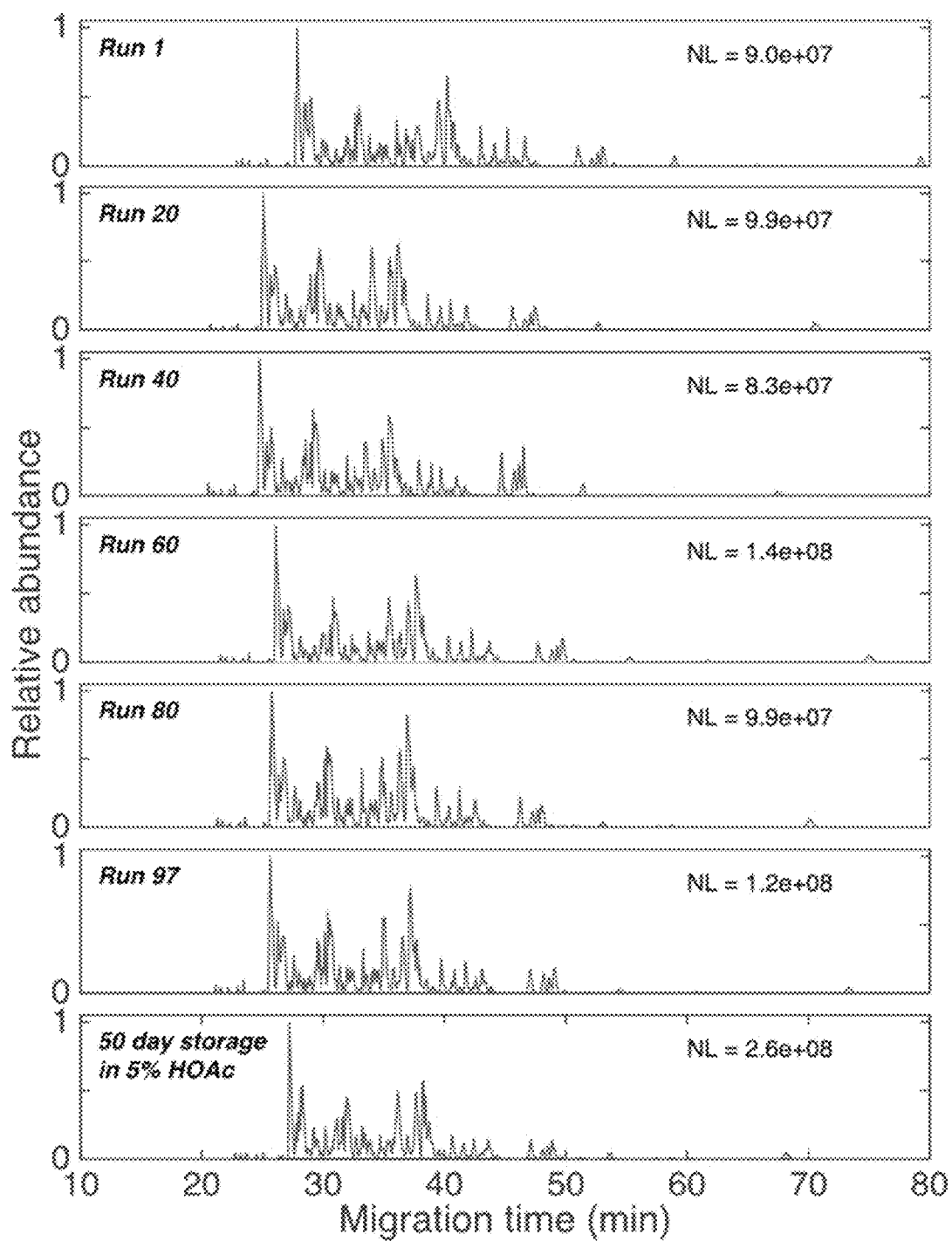
FIG. 1. Base peak electropherograms of BSA digests at selected runs and after storage for 50 days in 5% acetic acid. NL is the signal generated by the most intense peak in the base peak electropherogram, the normalization level.

The invention provides a novel catalyst free method for preparation of stable and reproducible linear polyacrylamide (LPA) coated capillaries. In the present invention a degassed polymerization solution containing a monomer, an initiator, and water is introduced into the capillary via vacuum. The capillary is then heated to thermally decompose the initiator, and allow the polymerization reaction to proceed. Because the polymerization is thermally initiated after the mixture is introduced into the capillary, the polymerization process can be controlled precisely and initiated simultaneously along the length of the capillary.

Proteomic analysis using CZE is typically performed with LPA coated capillaries. These capillaries minimize the adsorption of peptides and proteins to the inner wall of the capillary and decrease electroosmosis, which increases the separation capacity. Conventional LPA-coated capillary production is based on the use of TEMED to catalyze the free-radical polymerization that couples acrylamide to a pretreated capillary wall. The treated capillary is filled with a mixture of monomer, TEMED, and ammonium persulfate; with free radical polymerization beginning prior to introduction of the solution to the capillary. This previous method results in significant variation in the properties of LPA coated capillaries both along the length of the capillary and between lots. This variation is due to differences in the time between initiation of the reaction and the filling of the capillary.

The present invention relates to a method for the generation of stable and reproducible coatings. In the present invention, the monomer and initiator are mixed and introduced into the capillary without the TEMED catalyst. The mixture is stable and does not begin polymerization at room temperature (~22° C.). The capillary, now filled with the mixture, can then heated, for example, in a water bath, thereby initiating polymerization. This novel method of coating the inside of a capillary provides an inner coating in a more well-controlled manner. A mixture of four standard proteins was used to evaluate the coating performance. Compared with commercialized LPA capillaries, the LPA capillaries provided herein generate much better separation performance and superior protein peak shape in CZE analysis. We also analyzed an intact antibody (MW 150 k) by CZE-MS with the LPA capillary provided herein in triplicate runs. The intact antibody generated a Gaussian-shaped electrophoresis peak with 1.2% relative standard deviation in migration time and 8.5% in base peak intensity. An automated CZE-MS system was used to generate 97 successive separations of a BSA tryptic digest over 145 hrs. Separation efficiency averaged over 100,000 theoretical plates across this period with no systematic variation. The LPA coating protocol had excellent batch-to-batch reproducibility with relative standard deviation in migration time <7%, and in separation window <1%.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discussed above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change or separation, e.g., in a solution, in a reaction mixture, in a capillary, in vitro, or in vivo.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "run to run" refers to the consistency of performance, ideally here in data, results, and/or output of a sample, standard, test, and/or unknown, from a first injection and/or elution to a second injection and/or elution, and so on, of a capillary.

The term 'batch to batch" refers to the consistency of performance, ideally here in data, results, and/or output of a sample, standard, test, and/or unknown, from a first injection and/or elution to a second injection and/or elution, and so on, between two capillaries.

The term "catalyst" refers to a component of a reaction system that reduces the activation energy required for the reaction to proceed but does not change the overall Gibbs energy of the system. In certain embodiments, a catalyst requires heat greater than room temperature, or greater than about 30° C., to effectively catalyze a polymerization reaction within relevant time limits (e.g., a few minutes or one hour).

The term "initiator" refers to a component of a reaction system wherein the component is included in order to bring about a reaction or process, or some other reaction intermediates, including a chain reaction, and may or may not include a process for generating free radicals. An initiator may or may not be changed chemically and includes peroxides, azo compounds, Lewis acids, organometallic species or high energy irradiation, protonic acids, carbenium ions, onium ions, covalent initiators including alkylating agents, homoinitiaros, and electron transfer and/or nucleophilic attack initiators.

The term "resolution" is represented by $R_s$ and refers to a characteristic of a column, ideally here a capillary. Resolution measures the ability of a column, again ideally here a capillary, to separate components of an analyte, and is the difference between column retention times for peaks representing components of an analyte divided by their average widths.

The term "analyte migration" refers to variations in the retention time associated with components of an analyte from run to run and/or batch to batch.

Methods of the Invention

Preparation of LPA Coating.

Traditional methods for coating the inside of a capillary with LPA employs a mixture of an acrylamide monomer, TEMED catalyst, and an APS initiator. Typically, solutions of the three components, monomer, catalyst, and initiator are prepared individually. The solutions are then degassed with either nitrogen or helium. After the solutions are degassed, the APS and acrylamide monomer solutions are mixed. Once these solutions are mixed the TEMED solution is then added to the mixture and the solution containing the three components is vortexed. Addition of the TEMED catalyzes dissociation of APS. Dissociation of APS generates free radicals and thereby initiates the polymerization reaction. After the solution is vortexed, and therefore after polymerization begins, the mixture is introduced into the pretreated capillary. Using this method, polymerization is difficult to control; oxygen contamination is present during the TEMED addition step, and the polymerization reaction is not reproducible.

In the present invention, the need for TEMED is eliminated. In place of TEMED heat is used to dissociate APS and initiate polymerization. In addition, polymerization is initiated inside the capillary, and not outside of the capillary as is done using the traditional method. Capillaries resulting from the present invention have an improved coating uniformity, stability, reproducibility, resolution, and higher separation efficiency compared to commercial capillaries.

Stability.

CZE-ESI-MS analysis of 1 mg/mL of the BSA digest and four standard proteins mixture were used to evaluate the LPA coated capillaries described herein. The sample was dissolved in 10 mM $NH_4HCO_3$ to perform pH junction sample pre-concentration. An automated system was used to generate 97 consecutive separations of the BSA digest, FIG. 1. In this analysis, the sample was injected every 90 minutes for 145 hours of continuous separation; no rinse or regeneration step was performed between injections. The separation profile and base peak intensity are reasonably reproducible. The variation in migration time averaged <4% (RSD) across the 145 hour run. The peak area varied by 35% (RSD), which is typical for pressure-driven CZE injection.

Figure 2:
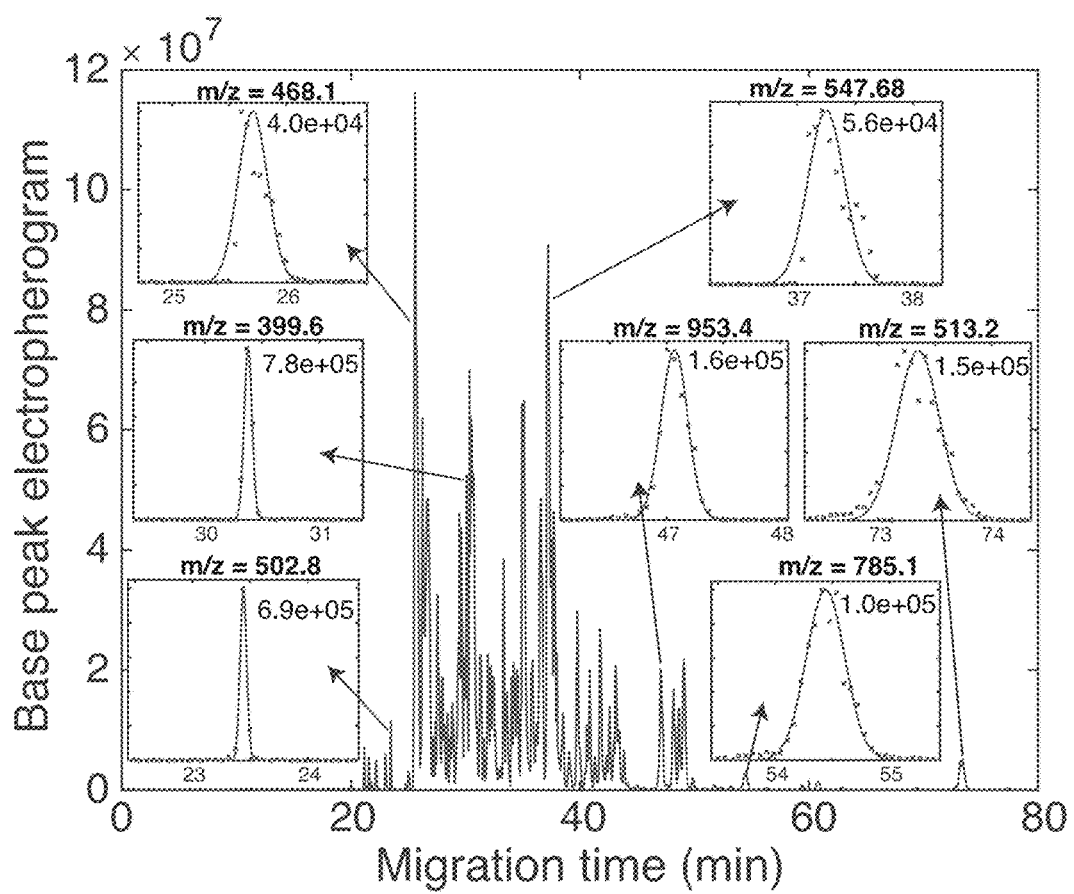
FIG. 2. Base peak electropherogram of a BSA digests generated after ~145 hours of continuous operation of a single coated capillary. Insets show selected ion electropherograms (SIEs) generated at the indicated m/z values. Data are shown as "x." The smooth curves in the inserts are the results of an unsupervised least-squares fit of a Gaussian function to the SIEs. Theoretical plate counts are shown for each SIE, based on the regression analysis. Median number of theoretical plates=125,000.

A set of seven selected ion electropherograms of a BSA digest, generated after ~145 hours of continuous operation of a single coated capillary were collected, FIG. 2. Plate counts range from 40,000 to 780,000, with a median plate count of 125,000, which is comparable to the best reports using commercial capillaries. The normalization level and signal amplitude roughly doubled after storage, which presumably reflects differences in sample concentration. A set of six selected ion electropherograms (SIEs) generated a median of 110,000 theoretical plates, identical to that produced by the first 97 runs before storage. A t-test was used to test the hypothesis that the migration times observed in runs 1-97 had the same mean value as were generated using the stored capillary; we could not reject this hypothesis (p<0.05) for four out of the six SIEs. The outstanding consistency of migration time and separation efficiency demonstrates the stability of this coating.

After the final injection, the capillary was stored for 50 days in 5% acetic acid, and another injection was performed. The bottom trace, FIG. 1, presents the electropherogram generated after storage. The consistent separation window further demonstrates the stability of this coating.

Intact Protein Separation.

Figure 3:
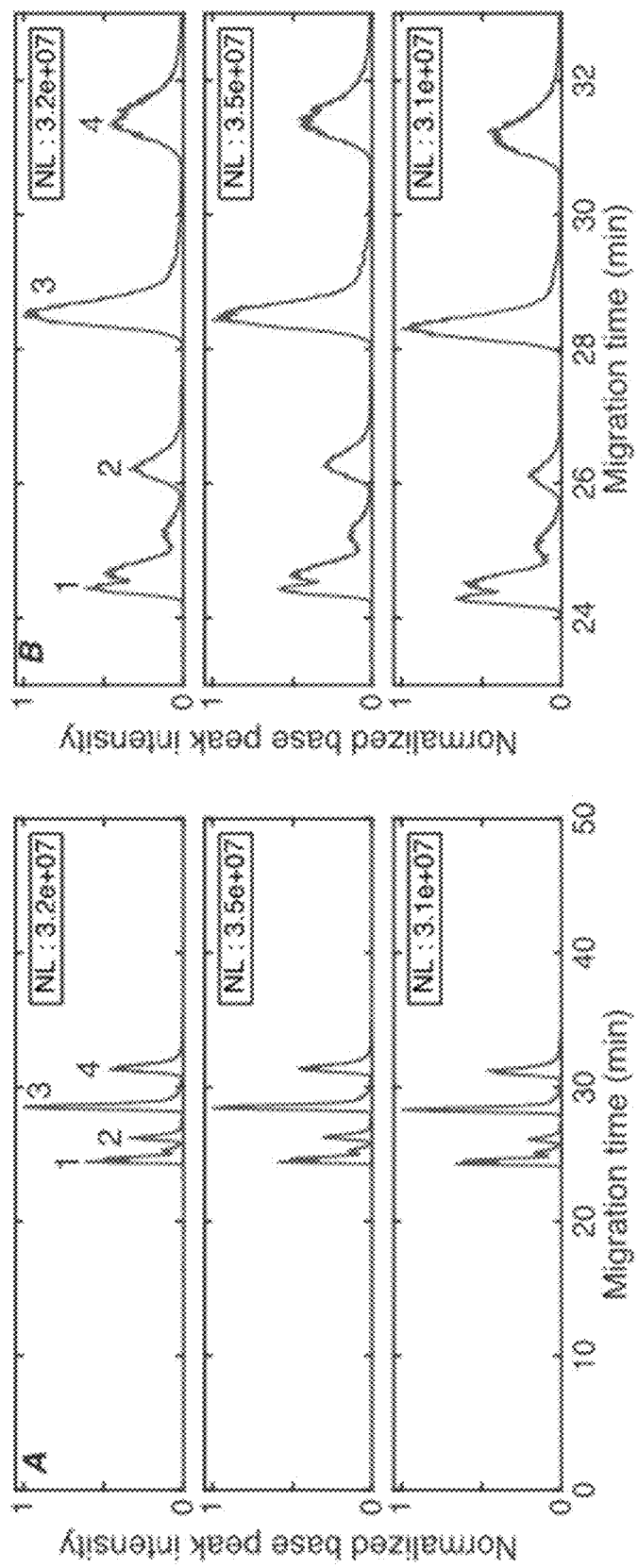
FIG. 3A-B. Base peak electropherograms of four standard proteins which includes A) a full run, and B) a close up of the region including the standard proteins, wherein peaks are representative of the following: 1) beta-lactoglobulin, 2) cytochrome C, 3) myoglobin, and 4) carbonic anhydrase, in triplicate runs. Data are treated with a Lowess filter with Gaussian kernel and 10 point span. NL is the normalization level, which is the maximum value of the filtered electropherogram. Experimental conditions: BGE: 5% acetic acid, separation voltage: 250 v/cm, sample matrix: 10 mM $NH_4HCO_3$ (pH 8), sample injection: 500 mbar for 0.2 min.
Figure 6:
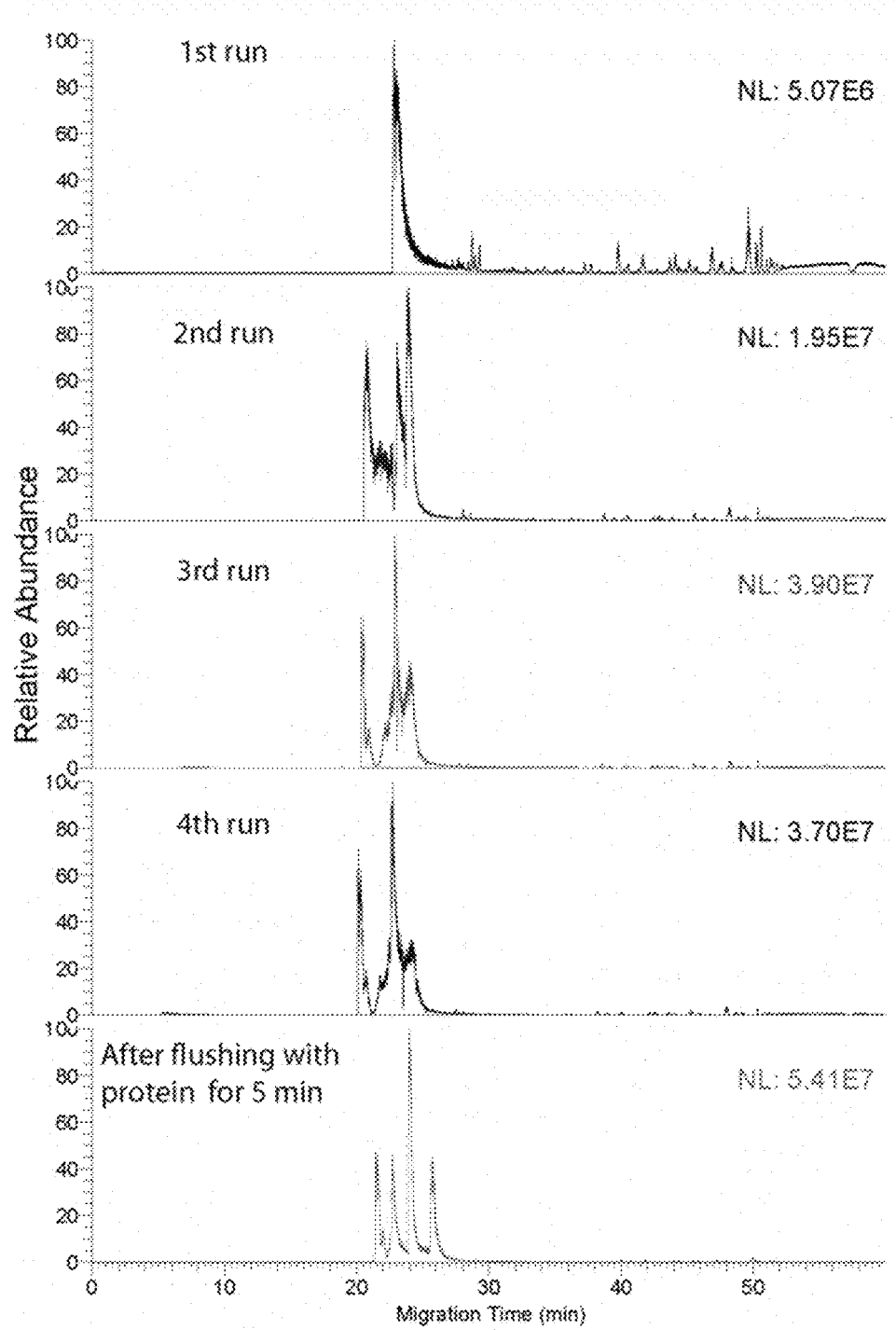
FIG. 6. Electropherograms of 4 standard proteins on commercial LPA capillary. Experimental conditions: BGE: 5% acetic acid, Separation voltage: 250 v/cm, sample matrix: 10 mM $NH_4HCO_3$ (pH 8), sample injection: 500 mbar for 0.3 min. NL is the normalization level, the signal generated by the most intense peak in the base peak electropherogram.

Triplicate electropherograms of a mixture of four standard proteins were collected, FIG. 3. Beta-lactoglobulin and its natural variants are separated into three peaks (with molecular weights 18542, 18628, and 18952) using a capillary coated with the thermally-initiated polymerization procedure. We also performed a separation of the same sample using a 1 m long piece of commercially-coated LPA capillary, FIG. 6.

Figure 7:
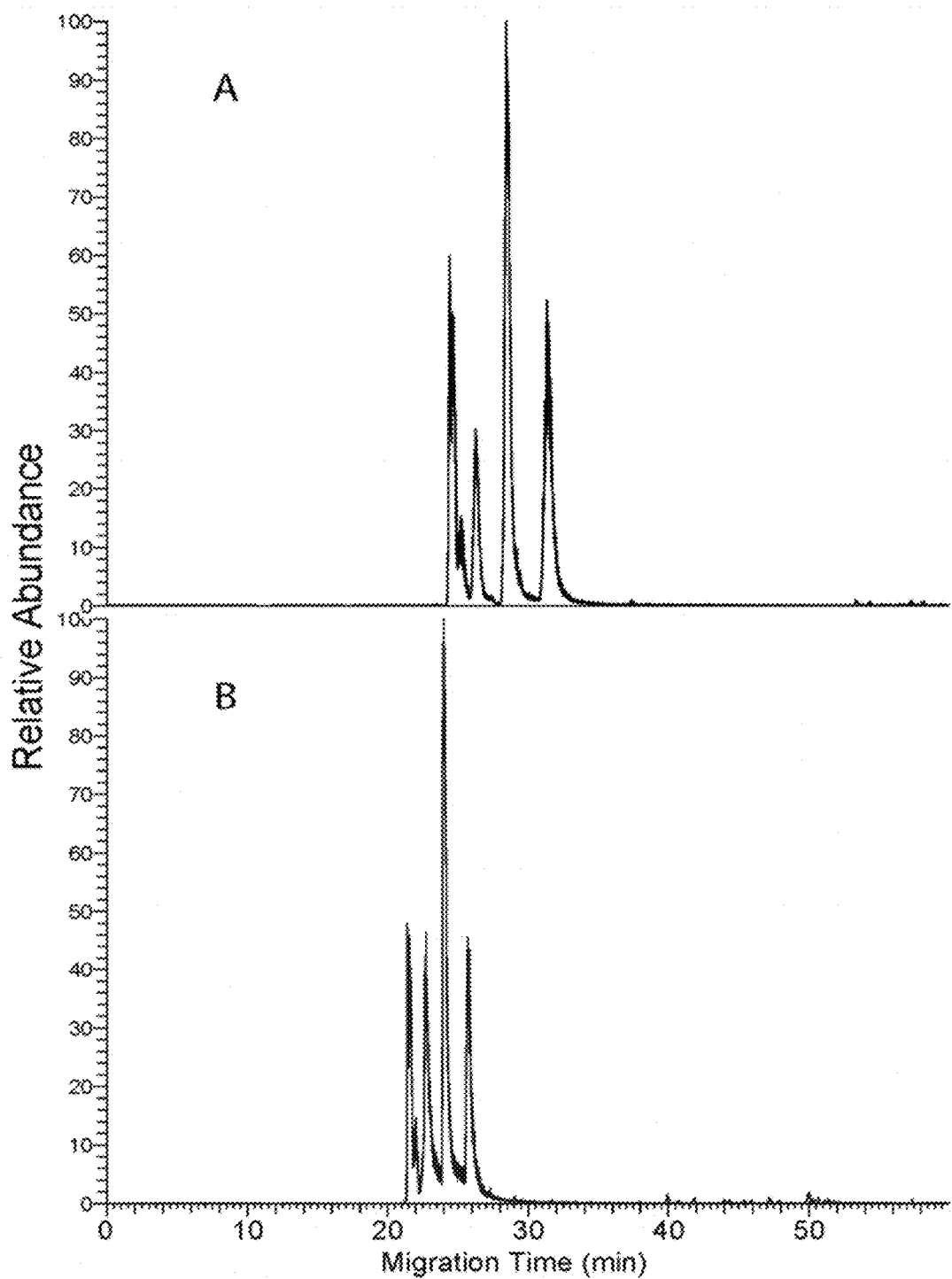
FIG. 7A-B. Electropherograms of 4 standard proteins by CZE-MS using (A) thermally-initiated LPA capillary (resolution of cytochrome c and myoglobin=2.6) and (B) commercial LPA capillary (resolution of cytochrome c and myoglobin=1.2) after protein coating. Experimental conditions: BGE: 5% acetic acid, Separation voltage: 250 v/cm, sample matrix: 10 mM $NH_4HCO_3$ (pH 8), sample injection: 500 mbar for 0.3 min.

The "1st run" generated a very small beta-lactoglobulin peak; instead most of proteins were adsorbed on the capillary wall. Subsequent injections generated increased peak intensities, but with poor separation performance and significant peak tailing. We assumed that active sites on the capillary wall bound to analyte, and that separation performance improved as those sites were covered by bound analyte. We observed that the separation performance improved after the commercial capillary was flushed with the protein mixture for 5 min, water for 10 min, and 5% acetic acid (BGE) for 10 min. As shown in bottom trace of FIG. 6, the four proteins can be resolved after this procedure. Nevertheless, the separation performance of the LPA-coated capillary prepared with thermally-initiated polymerization is still much better than commercial LPA capillary. The resolution of cytochrome c and myoglobin is 1.2 for commercially coated capillary and 2.6 using a capillary coated using the thermally-initiated polymerization procedure, FIG. 7.

Analysis of Intact Antibody.

Figure 4:
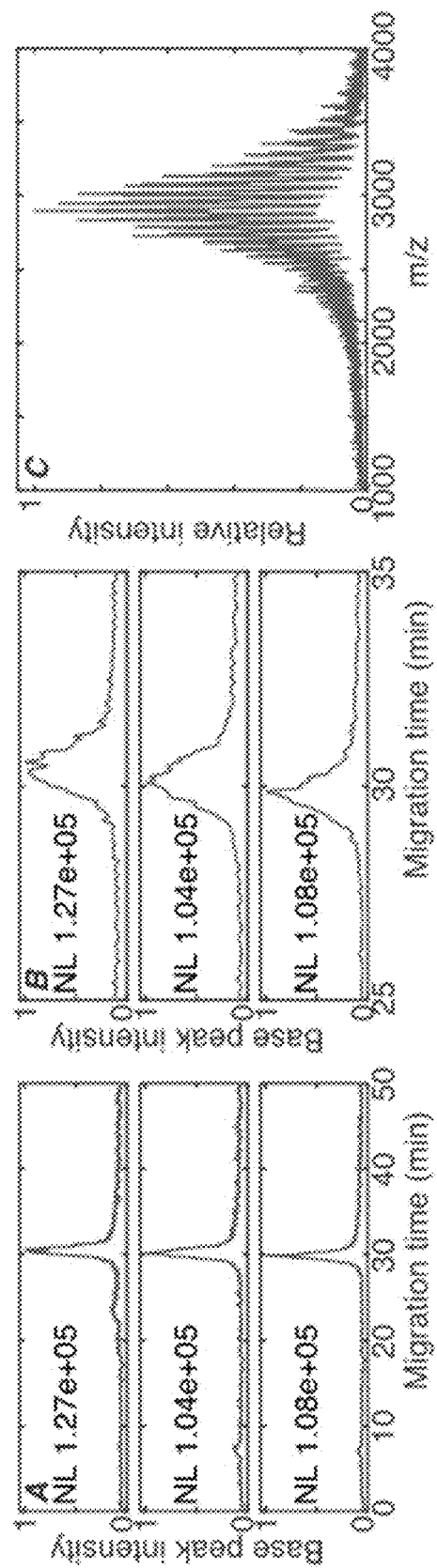
FIG. 4A-C. Base peak electropherograms in triplicate runs which includes A) a full run, B) a close up of the peak region, and C) a parent ion mass spectrum on intact antibody. For A and B, data are treated with a Lowess filter with Gaussian kernel and 10-point span. NL is the normalization level, which is the maximum value of the filtered electropherogram. For C, the parent ion mass spectra from 29.6 to 30.7 minutes were resampled at a common mass axis with 20,000 points between 1,000 and 4,000 Da. The spectra were then summed, the summed spectrum was treated with a Lowess filter with Gaussian kernel and 20-point span, and the averaged spectrum was normalized to unit height. Experimental conditions: BGE: 5% acetic acid, Separation voltage: 250 v/cm, sample matrix: 10 mM $NH_4HCO_3$ (pH 8), sample injection: 500 mbar for 0.3 min.

A 1.4 mg/mL solution of intact antibody (MW 150 kDa) was analyzed by CZE-MS using an LPA coated capillary described herein. FIGS. 4A and 4B show triplicate runs of intact antibody and FIG. 4C shows the parent ion spectrum. The electrophoretic peak is Gaussian, and displayed no tailing or fronting, and produced over 100,000 theoretical plates. The RSD of migration time and peak intensity are 1.2% and 8.5% respectively for the triplicate runs.

Reproducibility of the LPA Coating.

Figure 5:
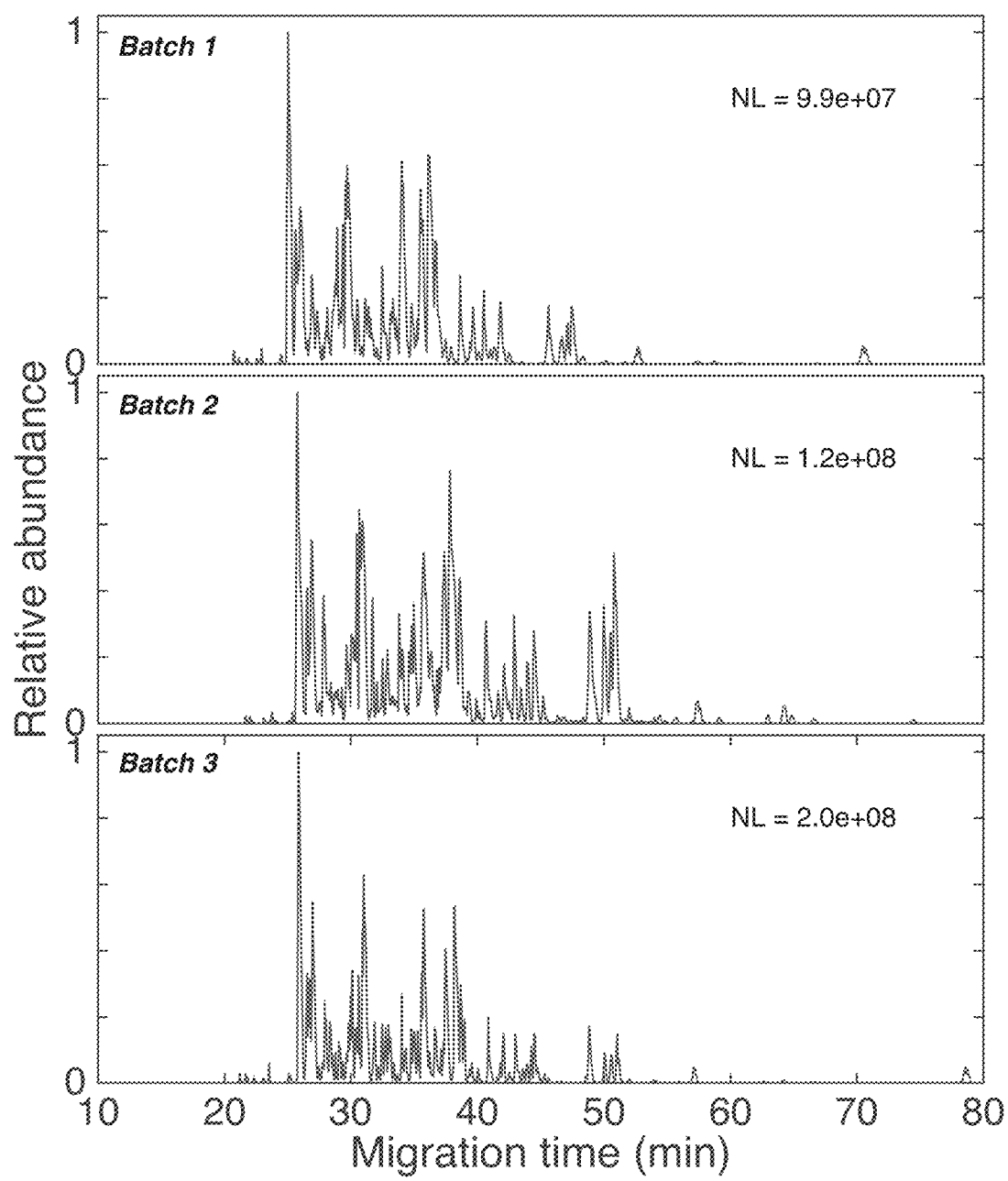
FIG. 5 Base peak electropherograms of BSA digests generated with capillaries taken from three batches of LPA coated capillary. NL is the normalization level, the signal generated by the most intense peak in the base peak electropherogram.

Finally, three batches of coating were prepared from two reels of uncoated capillaries, FIG. 5. The top two traces, "Batch 1" and "Batch 2" of FIG. 5, show the BSA digests analysis on capillaries taken from the first two batches, which were made from the same capillary reel. The bottom trace, "Batch 3," FIG. 5, shows the BSA digests analysis on a capillary taken from the third batch, made from another capillary reel. The separation profiles and separation windows are quite reproducible between batches. The relative standard deviation is 1% for the separation window, and <7% for migration time. Because the first two batches of LPA-coated capillaries were evaluated sequentially, they produced reproducible base peak intensity. The third LPA-coated capillary batch was evaluated 50 days after the first two, and difference in the base peak intensity is most likely due to changes in instrument conditions over this period.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Preparing a Coated Capillary

Figure 8:
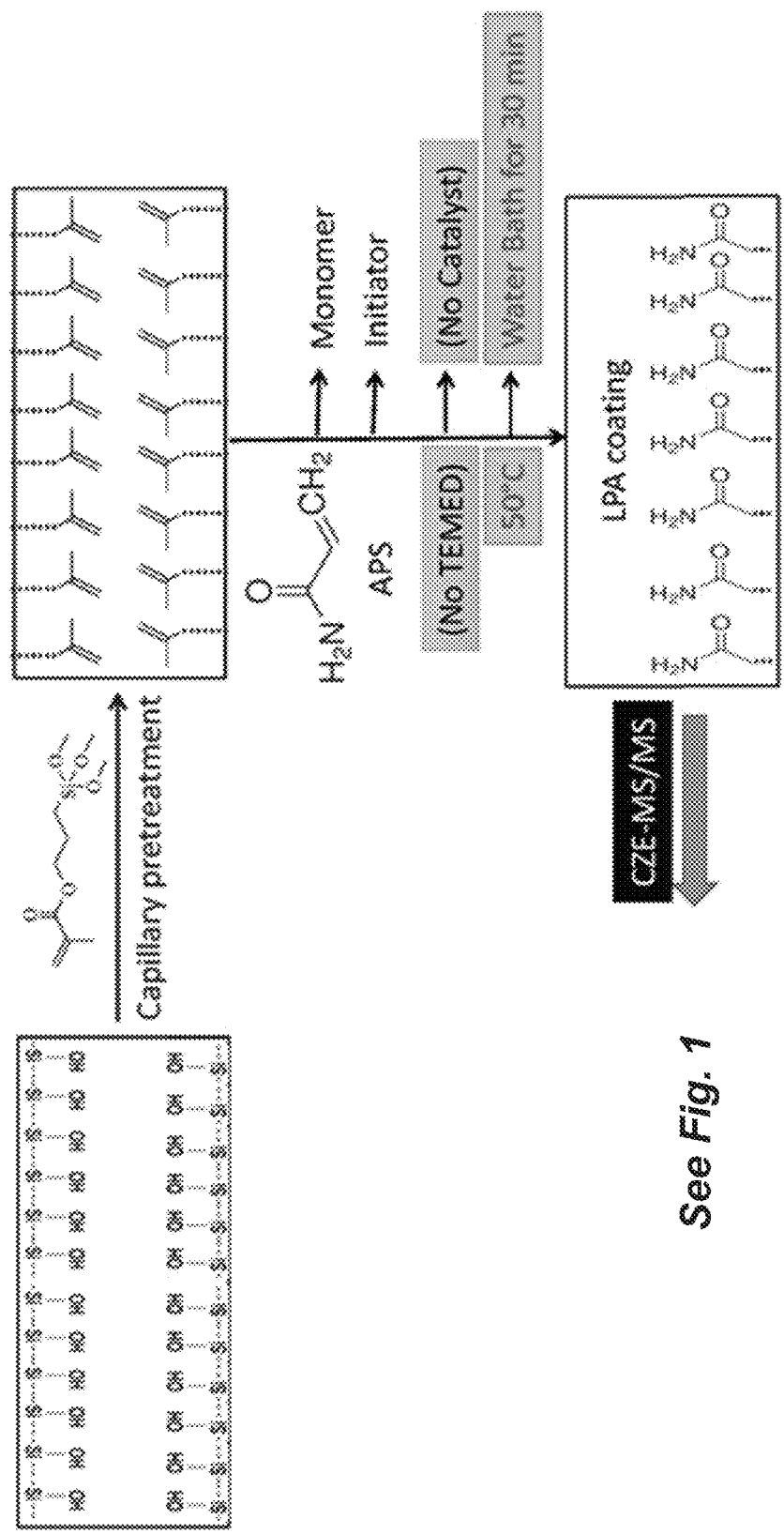
FIG. 8. A graphical abstract of the invention, according to one embodiment.

The following illustrates a process for preparing a coated capillary that eliminates the use of a catalyst (see FIG. 8).

An uncoated capillary was pretreated in the following manner. The capillary was flushed with 1 M HCl for 30 min, then water for 10 min, then 1 M NaOH for 30 min, then water for 10 min, and then MeOH for 30 min using a syringe pump at a flow rate of 2 µL/min. The flushed capillary was then dried under a flow of $N_{2(g)}$ at room temperature for 4 hr. The dried capillary was then flushed with 50% (v/v) 3-(trimethoxysilyl) propyl methacrylate in MeOH for 10 min. Both ends of the capillary were then sealed, and the now filled capillary was incubated at room temperature for 24 hr. Finally, the capillary was rinsed with MeOH for 20 min and dried under $N_{2(g)}$. The pretreated capillary was then stored at room temperature.

A pretreated capillary was coated in the following manner. First, 40 mg of acrylamide was dissolved in 1 mL water. And, 2 µL of 5% (w/v) ammonium persulfate (APS) was added to 500 µL of the acrylamide solution. The acrylamide/APS mixture was vortexed for 30 s and degassed for 5 min using $N_{2(g)}$. Then the mixture was then introduced into the pretreated capillary under vacuum. Both ends of the capillary were then sealed and the sealed capillary incubated in a 50° C. water bath for 30 min. Following incubation, the capillary was flushed with water to remove excess reagents, and was stored at room temperature. Prior to CZE-ESI-MS/MS experiments, a ~1-mm length of the distal tip of the capillary was etched with HF for 90 min. The resulting outer diameter of the etched end of the capillary had an outer diameter of ~70 µm.

Example 2. Methods for Analyzing Samples

The following illustrates a process for analyzing a sample on a capillary that has been coated by a process that eliminates the need for a catalyst.

A sample was prepared in the following manner. A 0.5 mg/mL solution of BSA in 100 mM $NH_4HCO_3$ (pH 8.0) containing 8 M urea was denatured at 37° C. for 30 min, followed by standard reduction and alkylation with DTT and IAA. Digestion was performed for 12 hours at 37° C. with trypsin at a trypsin/protein ratio of 1/30 (w/w). The digests were desalted followed by lyophilization with a vacuum concentrator. The dried samples were stored at −20° C. before use.

A mixture of standard proteins containing cytochrome c (0.05 mg/mL), myoglobin (0.15 mg/mL), beta-lactoglobulin (0.4 mg/mL) and carbonic anhydrase (0.15 mg/mL) dissolved in 10 mM $NH_4HCO_3$ (pH~8.5) buffer was prepared for dynamic pH junction based CZE-MS/MS analysis.

Three 10 µg aliquots of intact antibody solution were desalted. The sample was finally eluted into a 20 µL of 35% acetic acid with 50% ACN solution for CZE-MS analysis.

A PrinCE autosampler was used for automated sample injection and separation voltage control. A third-generation electrokinetically driven sheath-flow CE-MS nanospray interface was used to couple the separation with the mass spectrometer. A 5% acetic acid solution was used as the background electrolyte (BGE), and a 0.5% formic acid with 10% methanol was used as the sheath buffer. The nanospray high voltage was supplied by a Spellman CZE 1000R power supply. The emitter was pulled in a P-1000 Sutter pipette puller to a 25 µm o.d. tip. The nanospray voltage was ~2 kV. The separation was performed at 25,000 V across 1 m of LPA-coated capillary (250 V $cm^{-1}$). Sample injection was performed by pressure with 500 mbar for 0.2 min (injection volume 100 nL) for BSA digests and standard proteins and 500 mbar for 0.3 min for intact antibody injection. The LPA-coated separation capillary was coupled to a LTQ-XL (Thermo Fisher Scientific). Full MS scans were acquired over the 395-1900 m/z range for BSA digest analysis, 600-2000 for intact standard protein analysis and 600-4000 for intact antibody analysis.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method of coating the inside wall of a capillary with a polymeric material for capillary electrophoresis (CE), the method comprising:
   a) covalently grafting a vinyl group to the inside wall of an uncoated capillary to form a pretreated capillary;
   b) introducing a catalyst-free solution of a monomer and initiator, wherein the monomer is present at about 2% (w/v) to about 10% (w/v) and the initiator is present at about 0.1% (w/v) to about 1% (w/v), into the pretreated capillary and thermally initiating polymerization of the monomer, wherein the monomer forms a hydrophilic polymer upon polymerization;
   c) removing an excess of the solution thereby providing a hollow CE capillary comprising an internal polymeric coating for CE;
   wherein the internal polymeric coating is substantially linear, forms a covalent bond to the grafted vinyl group, and coats the inside wall of the hollow CE capillary.

2. The method of claim 1 wherein the monomer is present at about 4% (w/v).

3. The method of claim 1 wherein the initiator is present at about 0.2% (w/v).

4. The method of claim 1 wherein the initiator comprises a persulfate.

5. The method of claim 1 wherein the monomer is acrylamide.

6. The method of claim 1 wherein the catalyst-free solution is introduced into the pretreated capillary by vacuum.

7. The method of claim 1 wherein thermally initiating polymerization of the monomer comprises sealing both ends of the pretreated capillary and heating the pretreated capillary, wherein the catalyst-free solution is introduced into the pretreated capillary.

8. The method of claim 7 wherein thermally initiating polymerization is at about 40° C. to about 70° C.

9. The method of claim 1 wherein the resolution, $R_s$, of the CE capillary is improved by a factor of about 1.5 to about 2.5, compared to a capillary having a coating prepared by a catalyzed polymerization reaction.

10. The method of claim 1 wherein the reproducibility of analyte migration along the CE capillary is about 3% to about 5% run to run.

11. The method of claim 1 wherein the reproducibility of analyte migration along the CE capillary is about 6% to about 8% batch to batch.

12. The method of claim 1 wherein the relative standard deviation of the separation window is about 0.5% to about 1.5% batch to batch.

13. A method of coating the inside wall of a capillary with linear polyacrylamide (LPA) for capillary electrophoresis (CE), the method comprising:
   a) covalently grafting a vinyl-silane to the inside wall of an uncoated capillary to form a pretreated capillary;
   b) introducing a catalyst-free solution of acrylamide monomer and an initiator, wherein the monomer is present at about 2% (w/v) to about 10% (w/v) and the initiator is present at about 0.1% (w/v) to about 1% (w/v), into the pretreated capillary and thermally initiating polymerization of the monomer;
   c) removing an excess of the solution thereby providing a hollow CE capillary comprising an internal LPA coating for CE;
   wherein the internal LPA coating forms a covalent bond to the grafted vinyl-silane and coats the inside wall of the hollow CE capillary.

14. The method of claim 13 wherein the inside wall of the uncoated capillary is flushed with hydrochloric acid and sodium hydroxide prior to step a), and the vinyl silane is 3-(trimethoxysilyl)propyl methacrylate.

15. The method of claim 13 wherein the initiator comprises a persulfate.

16. The method of claim 13 wherein thermally initiating polymerization is at about 40° C. to about 70° C.

17. The method of claim 13 wherein the CE capillary has a median plate count of about 125,000 plates.

18. The method of claim 13 wherein the distal end of the CE capillary is etched.

19. The method of claim 18 wherein the distal end has an outer diameter of about 70 µm.

* * * * *